United States Patent
Camino et al.

(10) Patent No.: US 7,563,266 B2
(45) Date of Patent: *Jul. 21, 2009

(54) SLIDE AND KIT FOR DELIVERING IMPLANTS

(75) Inventors: Thomas S. Camino, Warsaw, IN (US); Anthony D. Zannis, Ft Wayne, IN (US); John W. Kemppainen, Richland, MI (US); Herbert E. Schwartz, Ft Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/610,287

(22) Filed: Jun. 30, 2003

(65) Prior Publication Data

US 2004/0267276 A1 Dec. 30, 2004

(51) Int. Cl.
*A61B 17/58* (2006.01)
*A61B 17/60* (2006.01)
*A61F 2/00* (2006.01)

(52) U.S. Cl. .................................................. 606/99

(58) Field of Classification Search ............ 104/69, 104/70; 238/10 R, 10 A, 10 F; 472/116; 606/99, 107, 96, 97; 600/201, 205, 216, 600/217; 623/13.12

See application file for complete search history.

(56) References Cited

U.S. PATENT DOCUMENTS

| | | | |
|---|---|---|---|
| 4,122,556 A * | 10/1978 | Poler | 623/6.12 |
| 4,349,027 A * | 9/1982 | DiFrancesco | 606/107 |
| 4,750,498 A * | 6/1988 | Graham | 600/587 |
| 4,836,202 A * | 6/1989 | Krasner | 606/107 |
| 4,873,976 A | 10/1989 | Schreiber | |
| 4,880,429 A | 11/1989 | Stone | |
| 4,981,841 A * | 1/1991 | Gibson | 514/2 |
| 5,007,934 A | 4/1991 | Stone | |
| 5,036,733 A * | 8/1991 | Tiholiz et al. | 76/119 |
| 5,108,421 A | 4/1992 | Fowler | |
| 5,108,438 A | 4/1992 | Stone | |
| 5,129,882 A | 7/1992 | Weldon | |
| 5,141,507 A * | 8/1992 | Parekh | 623/6.46 |
| 5,190,552 A * | 3/1993 | Kelman | 606/107 |
| 5,290,310 A | 3/1994 | Makower | |
| 5,306,311 A | 4/1994 | Stone | |
| 5,320,633 A | 6/1994 | Allen | |
| 5,320,639 A | 6/1994 | Rudnick | |
| 5,374,268 A | 12/1994 | Sander | |

(Continued)

OTHER PUBLICATIONS

O'Connor's Textbook of Arthroscopic Surgery, $2^{nd}$ ed., 1992, Chapter 19.

*Primary Examiner*—Anu Ramana

(57) ABSTRACT

A slide instrument has a longitudinal slide portion and spaced walls defining longitudinal channels. The slide instrument may be sized so that it can be inserted through standard arthroscopic portals to position the distal end of the slide instrument at a damaged tissue site. The slide instrument may be used to deliver an implant to the damaged tissue site. The implant has edges that fit within the longitudinal channels so that the implant can be moved along the slide portion to the distal end of the slide to deliver the implant to the damaged tissue site. The shape of the slide instrument protects the implant from damage as the implant is delivered from outside the patient's body to the damaged tissue site.

17 Claims, 12 Drawing Sheets

U.S. PATENT DOCUMENTS

| | | |
|---|---|---|
| 5,569,252 A | 10/1996 | Justin |
| 5,571,109 A * | 11/1996 | Bertagnoli ............... 606/61 |
| 5,653,715 A * | 8/1997 | Reich et al. ............. 606/107 |
| 5,681,353 A | 10/1997 | Li |
| 5,702,418 A | 12/1997 | Ravenscroft |
| 5,702,462 A | 12/1997 | Oberlander |
| 5,735,903 A | 4/1998 | Li |
| 5,873,906 A | 2/1999 | Lau |
| 5,919,225 A | 7/1999 | Lau |
| 5,951,587 A | 9/1999 | Qureshi |
| 5,968,052 A | 10/1999 | Sullivan |
| 5,980,524 A | 11/1999 | Justin |
| 5,984,926 A * | 11/1999 | Jones ..................... 606/72 |
| 5,993,475 A | 11/1999 | Lin |
| 6,015,429 A | 1/2000 | Lau |
| 6,042,582 A * | 3/2000 | Ray ........................ 606/61 |
| 6,042,610 A | 3/2000 | Li |
| 6,056,778 A | 5/2000 | Grafton |
| 6,152,935 A | 11/2000 | Kammerer |
| 6,156,044 A | 12/2000 | Kammerer |
| 6,176,880 B1 | 1/2001 | Plouhar |
| 6,238,402 B1 | 5/2001 | Sullivan |
| 6,280,449 B1 * | 8/2001 | Blake .................... 606/107 |
| 6,293,961 B2 | 9/2001 | Schwartz |
| 6,306,156 B1 | 10/2001 | Clark |
| 6,306,159 B1 | 10/2001 | Schwartz |
| 6,319,271 B1 | 11/2001 | Schwartz |
| 6,350,274 B1 | 2/2002 | Li |
| 6,391,051 B2 | 5/2002 | Sullivan |
| 6,491,697 B1 * | 12/2002 | Clark et al. ............ 606/107 |
| 6,572,626 B1 | 6/2003 | Knodel et al. |
| 6,605,093 B1 * | 8/2003 | Blake .................... 606/107 |
| 6,652,561 B1 | 11/2003 | Tran |
| 6,770,078 B2 * | 8/2004 | Bonutti ................... 606/88 |
| 6,929,606 B2 * | 8/2005 | Ritland ................... 600/201 |
| 2001/0023352 A1 | 9/2001 | Gordon |
| 2004/0267277 A1 * | 12/2004 | Zannis et al. ............ 606/99 |

* cited by examiner

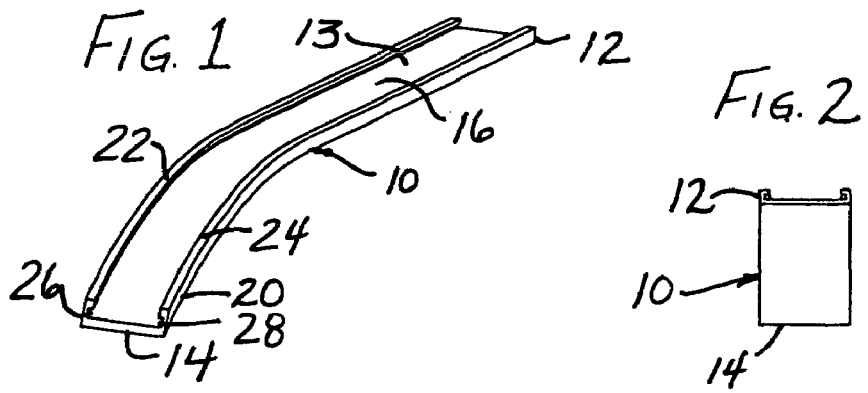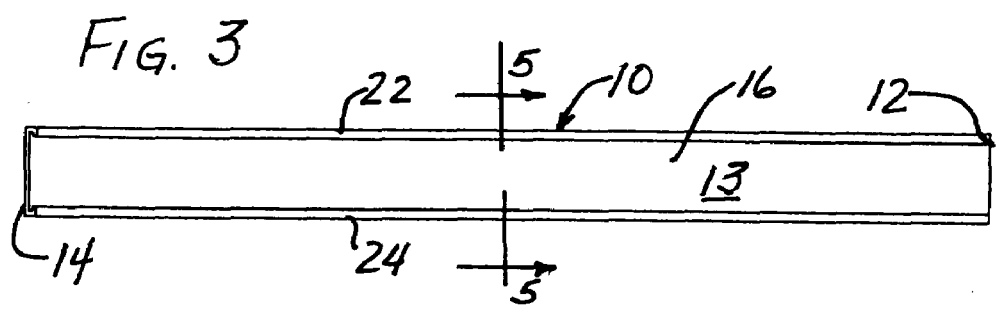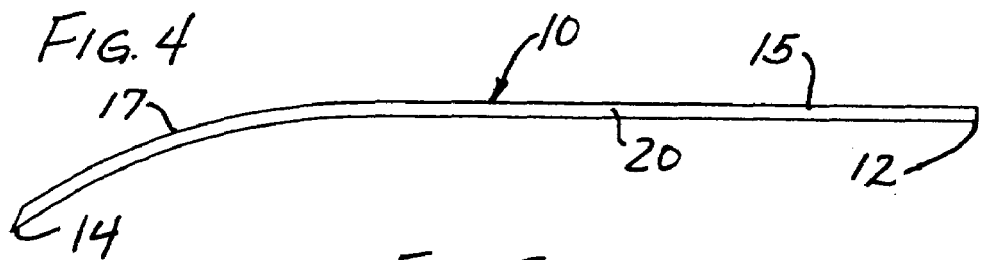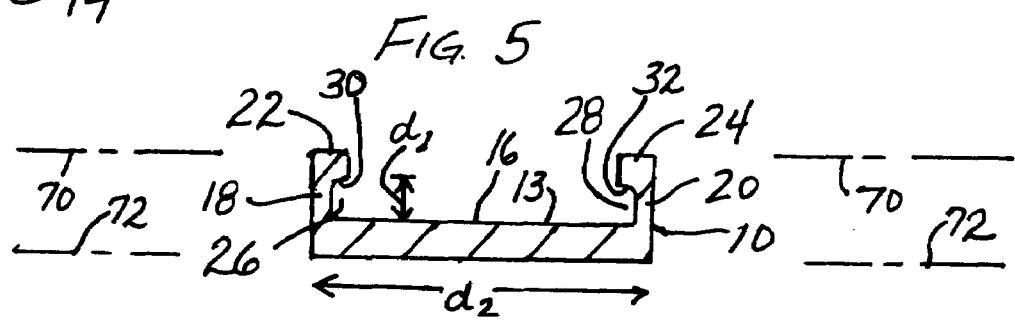

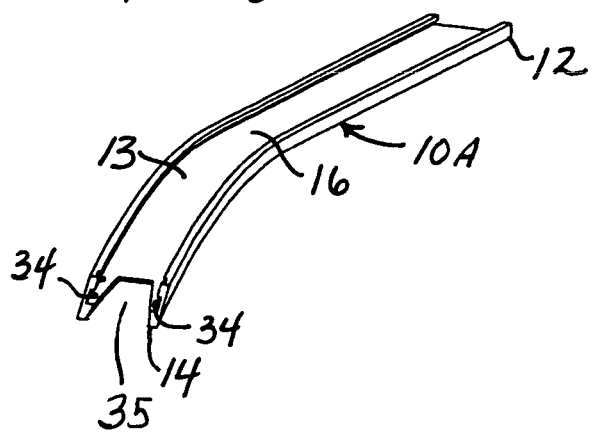
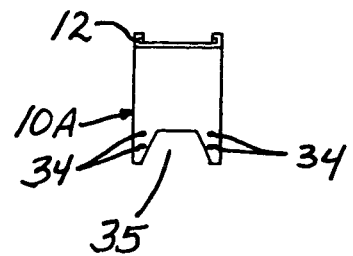
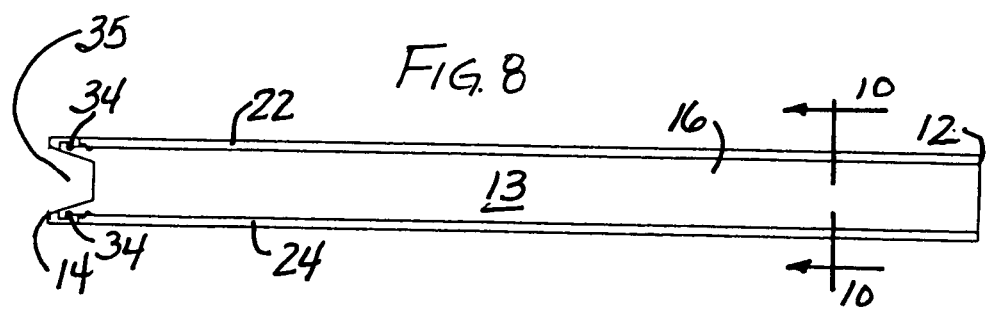
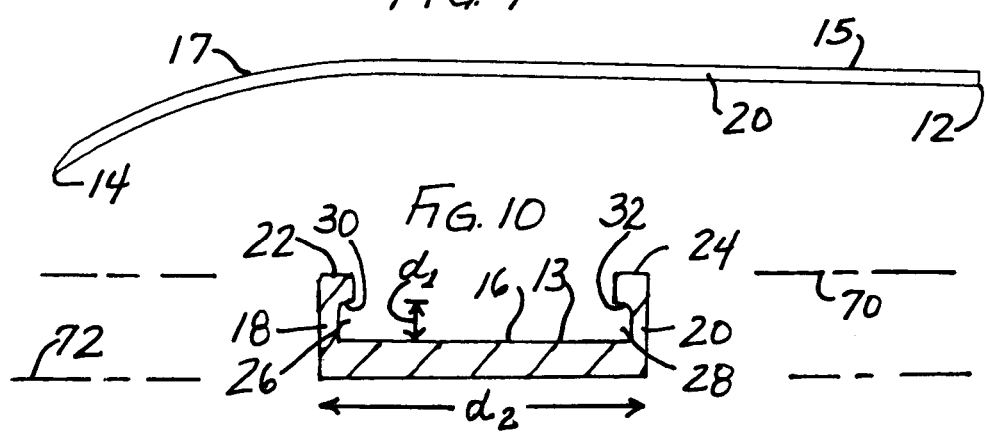

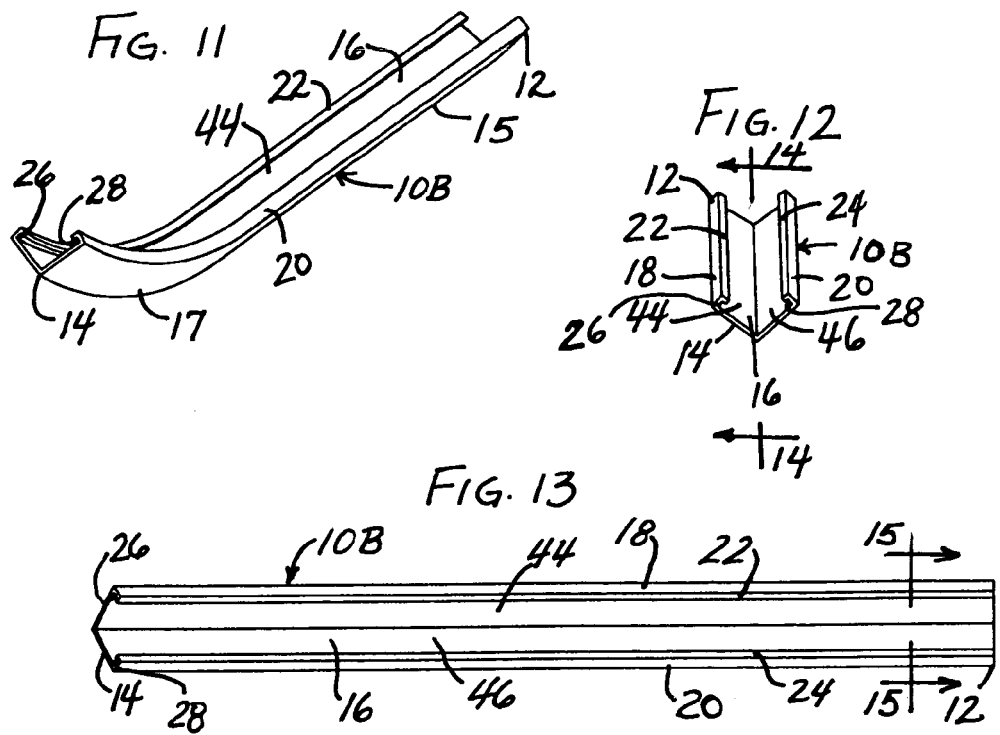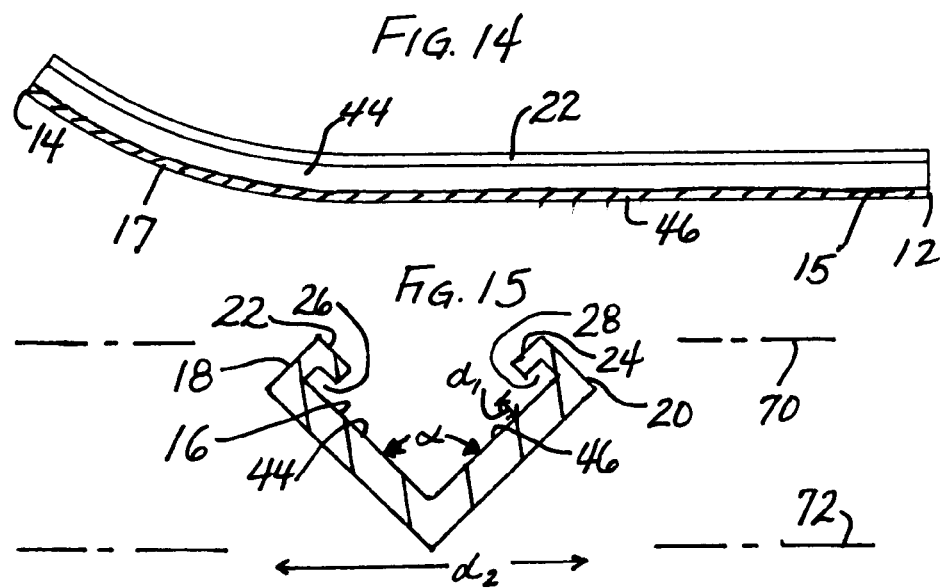

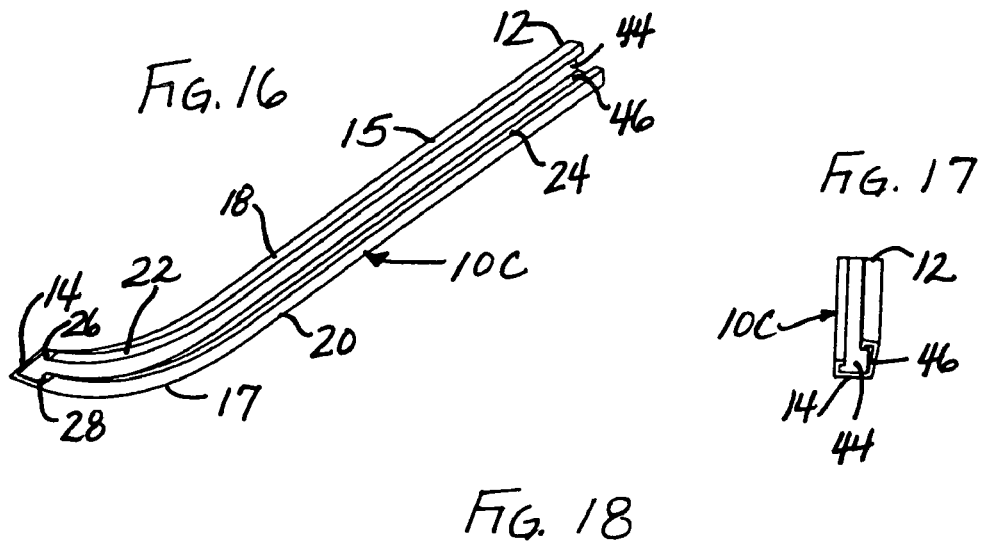
FIG. 16
FIG. 17
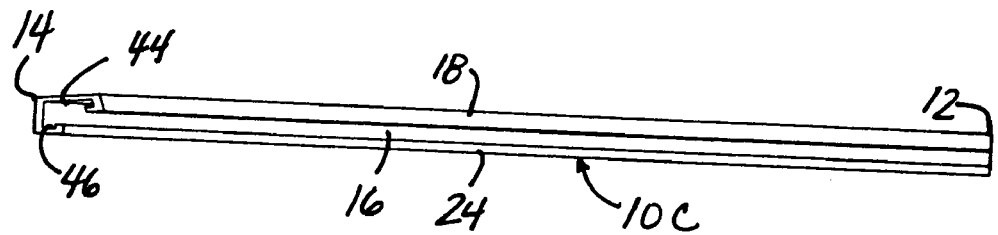
FIG. 18
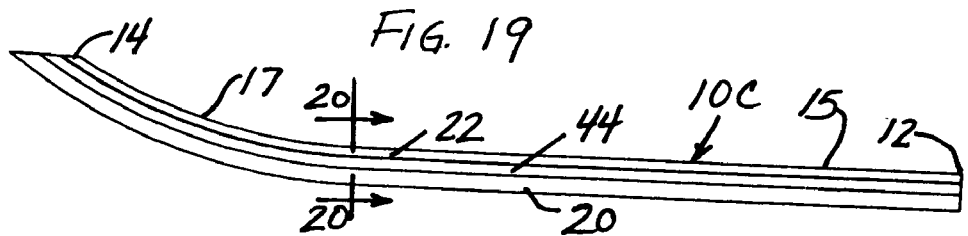
FIG. 19
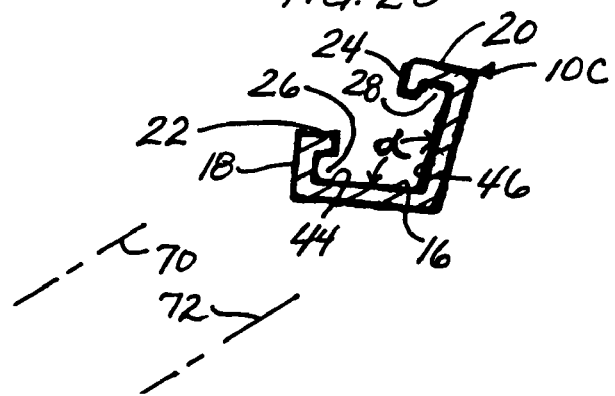
FIG. 20

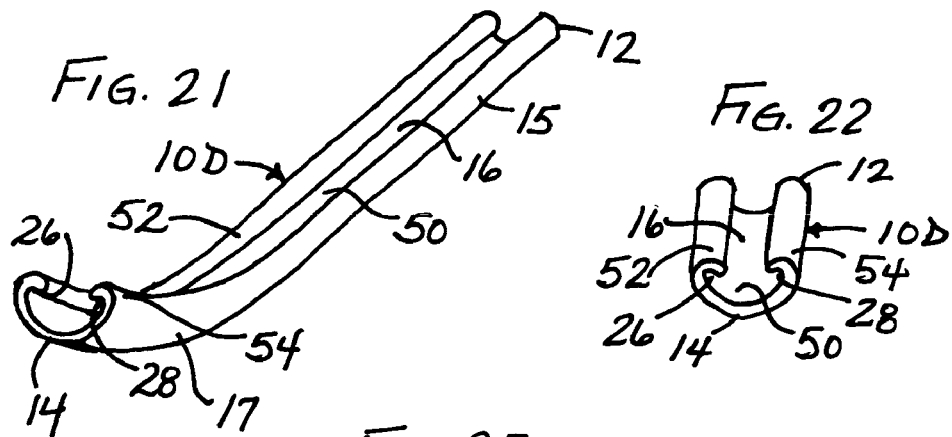
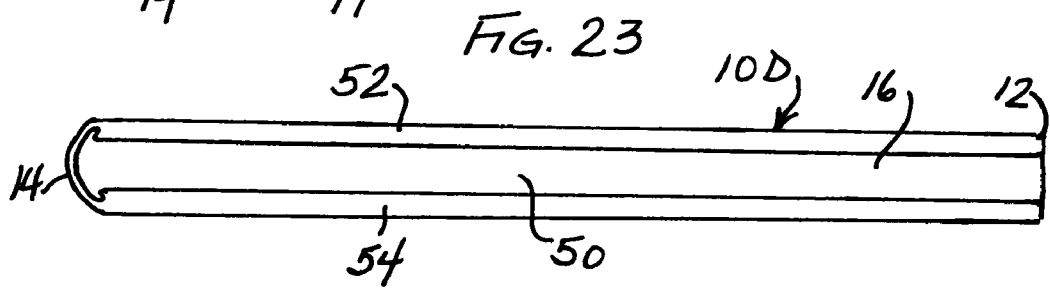
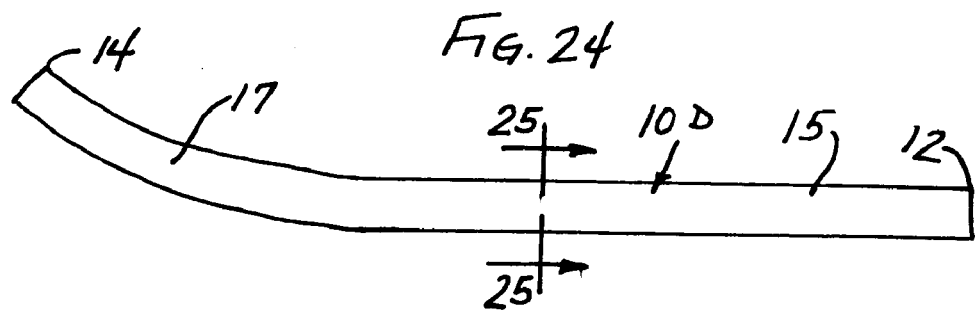
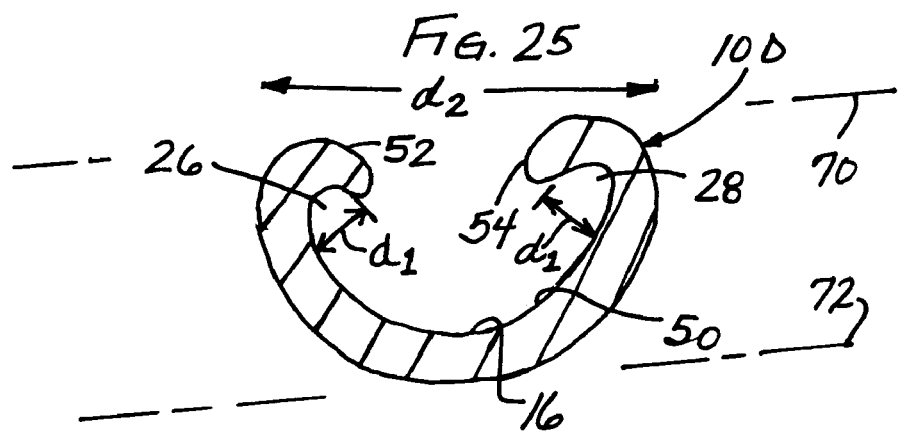

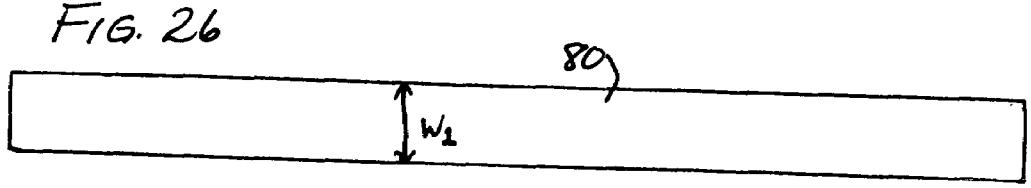
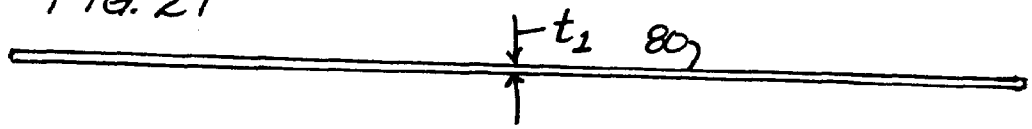
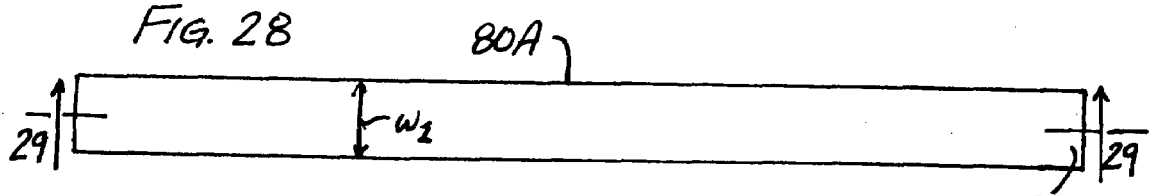
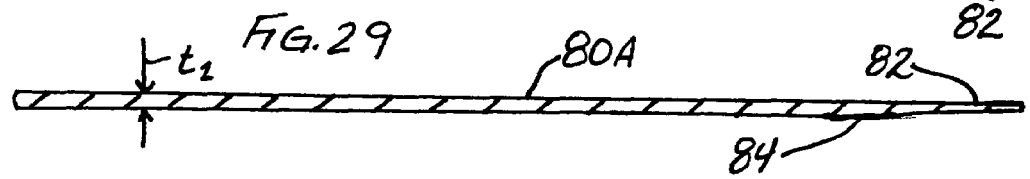
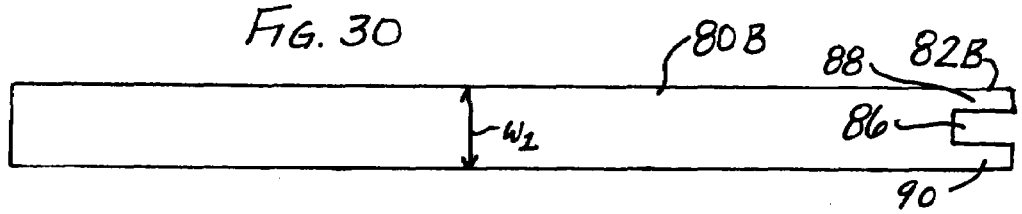
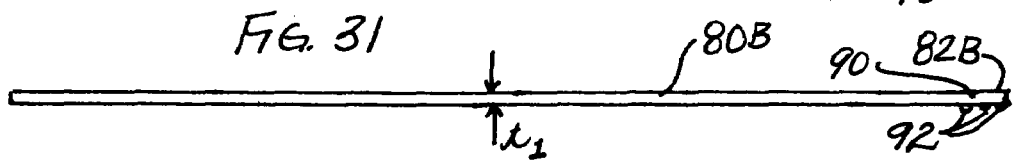

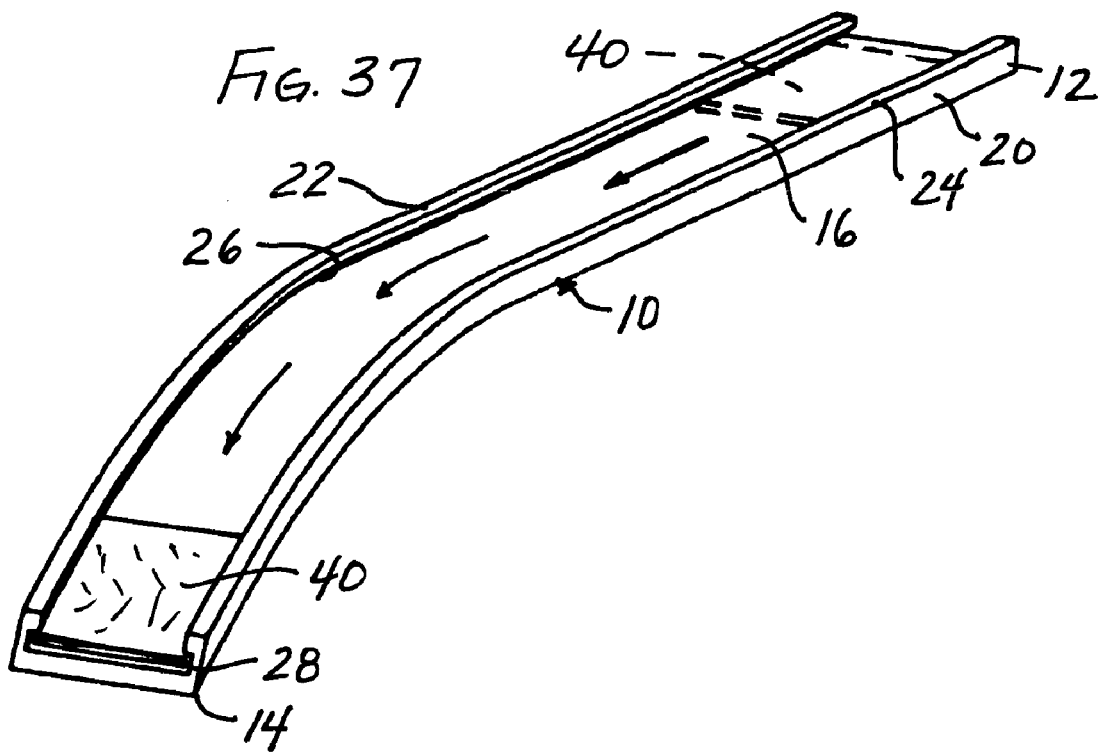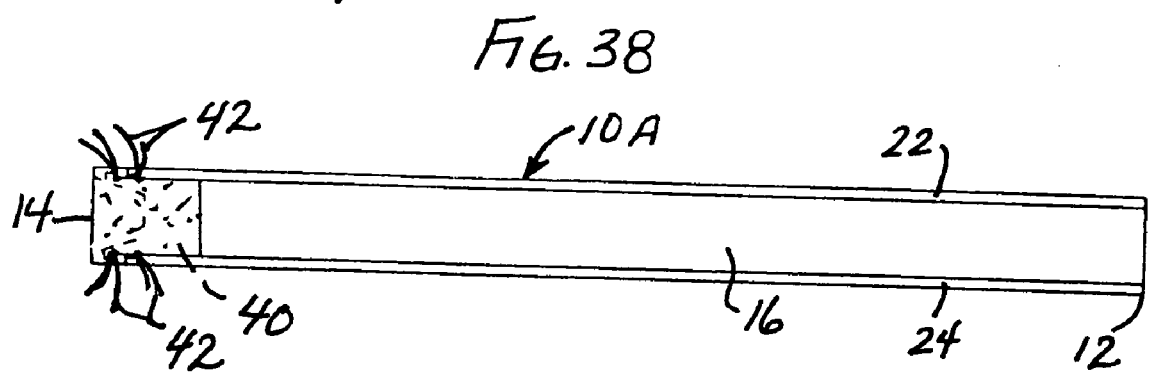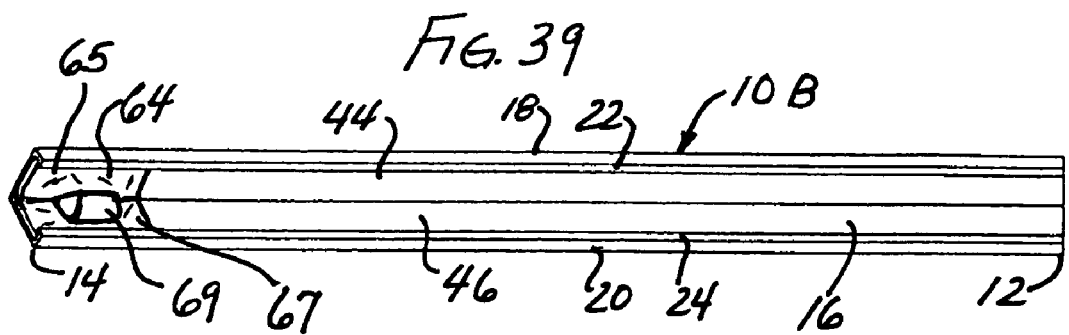

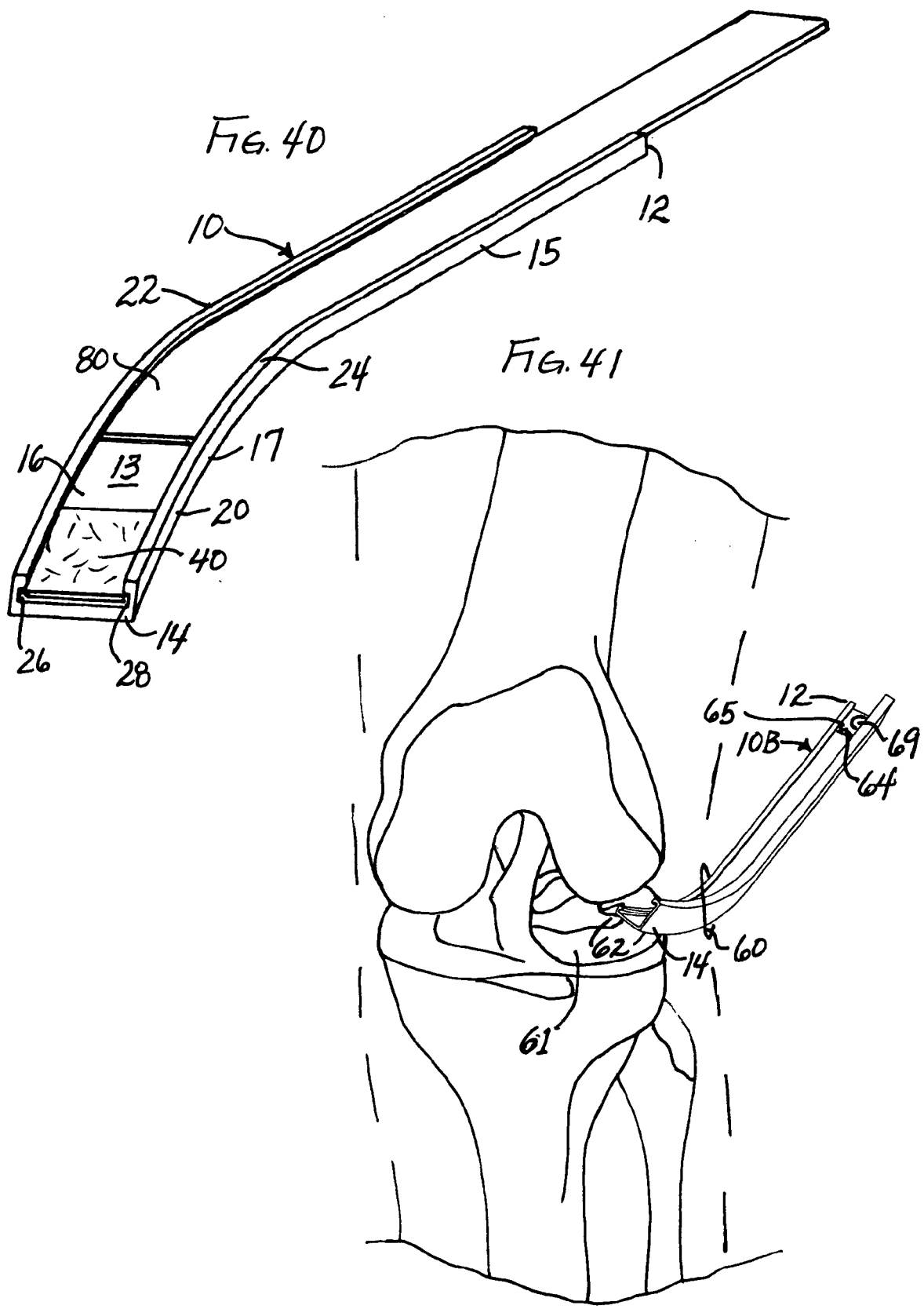

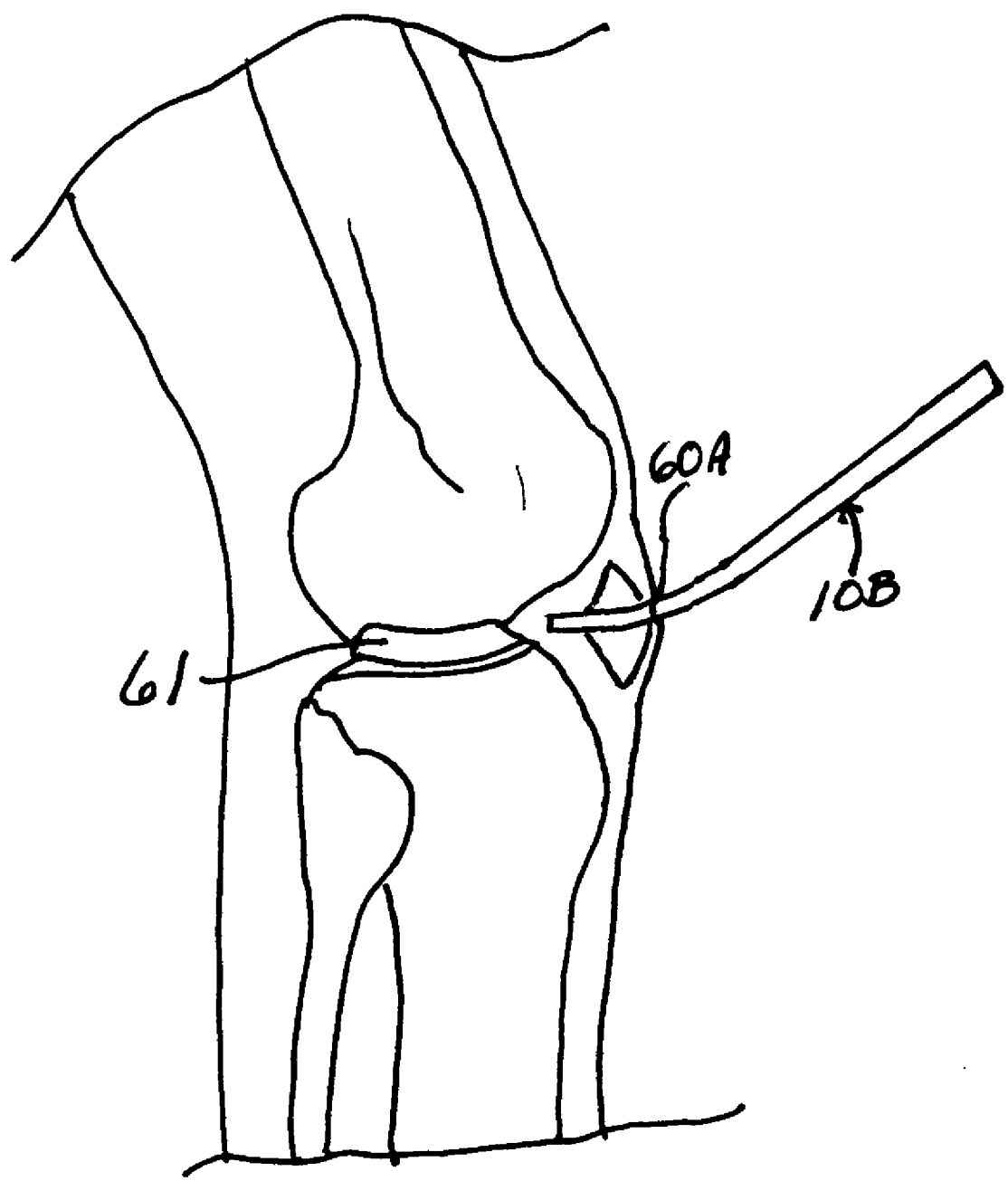

SLIDE AND KIT FOR DELIVERING IMPLANTS

FIELD OF THE INVENTION

The present invention relates generally to devices and kits for delivering an implant to a damaged tissue site.

BACKGROUND OF THE INVENTION

Human joints have a type of cartilage known as intra-articular fibrocartilage. Intra-articular fibrocartilage can be present in the form of a discus articularis, that is, as a plate or ring of fibrocartilage in the joint capsule separating the joint surfaces (articular cartilage) of the bones of the joint. Such fibrocartilage is present, for example, in the temporomandibular joint, between vertebrae, and in the knee joint. In the knee joint, the intra-articular fibrocartilage comprises the meniscus, a crescent-shaped or semi-lunar-shaped disc of tissue that is located between the femoral condyles and the tibial plateau. The meniscus primarily functions as a shock absorber, absorbing the shock of compressive and shear forces in the knee. The meniscus also provides a substantially frictionless surface for articulation of the knee joint.

When cartilage tissue is no longer healthy, there can be debilitating pain in the joint. Cartilage health can be adversely affected by disease, aging, or trauma. The adverse effects of disease, aging and trauma can be in the form of a tear in the cartilage or in the form of a breakdown of the cartilage matrix.

In the knee, the meniscus is frequently damaged in twisting injuries. It is also damaged with repetitive impact over time. Meniscus degeneration can also occur by aging; as a person ages, the meniscus can become mechanically compromised in places, so that even common motions like squatting can cause meniscal tears.

Common surgical procedures for treating meniscal damage include tear repairs and menisectomies. A tear repair is most commonly performed when the tear is a clean longitudinal vertical lesion in the vascular "red" or "pink" zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos. 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Menisectomies involve the surgical removal of part of the meniscus. Such procedures have generally been performed in cases of radial tears, horizontal tears, vertical longitudinal tears outside the vascular zone, complex tears, or defibrillation. Although menisectomies provide immediate relief to the patient, in the long term the absence of part of the meniscus can cause cartilage wear on the condylar surface, eventually leading to arthritic conditions in the joint.

Such surgical procedures are commonly performed arthroscopically. In arthroscopy, small incisions are made at the affected joint to form portals for the insertion of instruments, including a small lens and lighting system (an arthroscope). The arthroscope is connected to a viewing device, such as a television monitor to allow the surgeon to see the interior of the joint. Other instruments are inserted through other portals to perform a variety of tasks. For example, the surgical instrument may include an implement for manipulating native tissue (for example, tissue grasping, tissue cutting, bone abrading).

Typical surgical instruments used in arthroscopic procedures include rongeurs, such as the Kerrison rongeur, punch forceps, basket forceps, suction punches and cup curet, for example. Examples of arthroscopic instruments are described and illustrated in O'Connor's Textbook of Arthroscopic Surgery, $2^{nd}$ ed., 1992, Chapter 19.

Other common surgical techniques in orthopaedic surgery include open surgery and mini-arthrotomy. For example, for knee surgery, the surgery may be performed by an open knee arthrotomy, where the incision may typically be 20-30 cm in length, and wherein the patella is everted during surgery. Knee surgery may also be performed by a mini-knee arthrotomy, where the incision is typically 10-13 cm in length and patella tension is avoided.

Another common site of soft tissue injury and degeneration is the rotator cuff in the shoulder. The rotator cuff comprises the tendons that attach muscles to a bone in the shoulder. Where one of the tendons is thin, delaminated or frayed to the point that surgical repair or reconstruction is necessary, the damaged tendon can be reinforced with graft tissue or with an orthopaedic implant.

SUMMARY OF THE INVENTION

The present invention is directed toward devices and kits for the delivery of implants to a damaged tissue site (such as the intra-articular space in the area of the meniscus in the human knee joint) so that the implants can be used to approximate, repair or regenerate damaged or diseased tissue at the site.

In one aspect, the present invention provides a slide for delivering an implant to a damaged tissue site in a patient's body. The slide comprises a proximal end, a distal end and an elongate longitudinal slide portion between the proximal and distal ends. The slide also has walls defining spaced longitudinal channels along the longitudinal slide portion. The channels are sized and shaped so that a portion of the implant can be received within each channel. The slide has a longitudinal profile including a curved portion at the distal end and a straight portion at the proximal end.

In another aspect, the present invention provides a surgical kit for delivering an implant to a damaged tissue site in a patient's body. The kit comprises an elongate guide member and a slide. The slide has a proximal end, a distal end and a longitudinal slide portion between the proximal and distal ends. The longitudinal slide portion has walls defining integral spaced longitudinal channels. The elongate guide member and longitudinal channels are complementary so that parts of the elongate guide member are receivable in the longitudinal channels. The elongate guide member is slidable in the longitudinal channels in a proximal-distal direction and the longitudinal channels constrain movement of the elongate guide member to sliding in the proximal-distal direction.

In another aspect, the present invention provides a surgical kit for delivering an implant to a damaged tissue site in a patient's body. The kit comprises an elongate guide member and a slide for delivering an implant to the damaged tissue site. The elongate guide member has a proximal end and a distal end. The slide comprises a proximal end, a distal end and a longitudinal slide portion between the proximal and distal ends. At least one of the elongate guide member and the slide has walls defining integral spaced longitudinal channels. The elongate guide member has a maximum transverse dimension so that the distal end of the elongate guide member can be introduced arthroscopically to the damaged tissue site. The slide also has a maximum transverse dimension so that the distal end of the slide can be introduced arthroscopically to the damaged tissue site. The elongate guide member and slide have complementary structures to allow the elongate guide member and slide to be connected to each other while allowing relative movement between the elongate guide member and slide in the proximal-distal direction while the elongate guide member and slide are connected.

BRIEF DESCRIPTION OF THE DRAWINGS

The invention will be better understood by reference to the figures of the drawings wherein like numbers denote like parts throughout and wherein:

FIG. 1 is a perspective view of a first embodiment of an arthroscopic slide embodying the principles of the present invention;

FIG. 2 is an end elevation of the arthroscopic slide of FIG. 1, taken from the proximal end of the arthroscopic slide;

FIG. 3 is a top plan view of the arthroscopic slide of FIGS. 1 and 2;

FIG. 4 is a side elevation of the arthroscopic slide of FIGS. 1-3;

FIG. 5 is a cross-section of the arthrosccopic slide of FIGS. 1-4, taken along line 5-5 of FIG. 3;

FIG. 6 is a perspective view of a second embodiment of an arthroscopic slide embodying the principles of the present invention;

FIG. 7 is an end elevation of the arthroscopic slide of FIG. 6, taken from the proximal end of the arthroscopic slide;

FIG. 8 is a top plan view of the arthroscopic slide of FIGS. 6 and 7;

FIG. 9 is a side elevation of the arthroscopic slide of FIGS. 6-8;

FIG. 10 is a cross-section of the arthroscopic slide of FIGS. 6-9, taken along line 10-10 of FIG. 8;

FIG. 11 is a perspective view of a third embodiment of an arthroscopic slide embodying the principles of the present invention;

FIG. 12 is an elevation of the arthroscopic slide of FIG. 11, taken from the distal end of the arthroscopic slide;

FIG. 13 is a top plan view of the arthroscopic slide of FIGS. 11 and 12;

FIG. 14 is a cross-section of the arthroscopic slide of FIGS. 11-13, taken along line 14-14 of FIG. 12;

FIG. 15 is a cross-section of the arthroscopic slide of FIGS. 11-14, taken along line 15-15 of FIG. 13;

FIG. 16 is a perspective view of a fourth embodiment of an arthroscopic slide embodying the principles of the present invention;

FIG. 17 is an end elevation of the arthroscopic slide of FIG. 16, taken from the distal end of the arthroscopic slide;

FIG. 18 is a top plan view of the arthroscopic slide of FIGS. 16 and 17;

FIG. 19 is a side elevation of the arthroscopic slide of FIGS. 16-18;

FIG. 20 is a cross-section of the arthroscopic slide of FIGS. 16-19, taken along line 20-20 of FIG. 19;

FIG. 21 is a perspective view of a fifth embodiment of an arthroscopic slide embodying the principles of the present invention;

FIG. 22 is an end elevation of the arthroscopic slide of FIG. 21, taken from the distal end of the arthroscopic slide;

FIG. 23 is a top plan view of the arthroscopic slide of FIGS. 21 and 22;

FIG. 24 is a side elevation of the arthroscopic slide of FIGS. 21-23;

FIG. 25 is a cross-section of the arthroscopic slide of FIGS. 21-24, taken along line 25-25 of FIG. 24;

FIG. 26 is a top plan view of a first embodiment of an elongate guide member that may be used with the arthroscopic slide of the present invention;

FIG. 27 is a side elevation of the elongate guide member of FIG. 26;

FIG. 28 is a top plan view of a second embodiment of an elongate guide member that may be used with the arthroscopic slide of the present invention;

FIG. 29 is a cross-section of the elongate guide member of FIG. 28, taken along line 29-29 of FIG. 28;

FIG. 30 is a top plan view of a third embodiment of an elongate guide member that may be used with the arthroscopic slide of the present invention;

FIG. 31 is a side elevation of the elongate guide member of FIG. 30;

FIG. 37 is a perspective view of the arthroscopic slide of FIGS. 1-5 and an implant, showing two positions of the implant on the slide and the direction of movement of the implant on the slide;

FIG. 38 is a top plan view of the arthroscopic slide of FIGS. 6-10 and an implant temporarily attached to the distal end of the slide with sutures;

FIG. 39 is a top plan view of the arthroscopic slide of FIGS. 11-15 with an implant at the distal end of the slide;

FIG. 40 is a perspective view of the arthroscopic slide of FIGS. 1-5 with an implant at its distal end and with an elongate guide member received in the channels of the arthroscopic slide;

FIG. 41 is a diagrammatic anterior view of the intra-articular space of a human knee joint with the arthroscopic slide of FIGS. 11-15 carrying an implant, illustrating insertion of the distal end of the arthroscopic slide through an arthroscopic portal into the intra-articular space to deliver the implant to the intra-articular space; and FIG. 42 is a diagrammatic side view of a human knee joint with the arthroscopic slide of FIGS. 11-15, illustrating insertion of the distal end of an anterior arthroscopic portal to deliver the implant to the intra-articular space.

DETAILED DESCRIPTION OF THE ILLUSTRATED EMBODIMENTS

Figure 32:
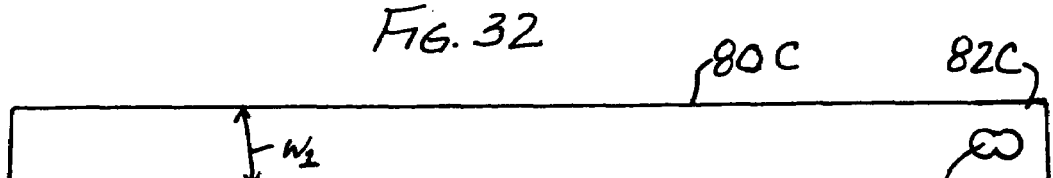
FIG. 32 is a top plan view of a fourth embodiment of an elongate guide member that may be used with the arthroscopic slide of the present invention.

A variety of orthopaedic implants useful in approximating, repair or regeneration of fibrocartilage are disclosed in the following applications for U.S. Ser. No. 10/195,794 entitled "Meniscus Regeneration Device and Method"; Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; Ser. No. 10/195,633 entitled "Porous Delivery Scaffold and Method", each of which is assigned to the same assignee as the present application, each of which was filed on Jul. 15, 2002, and each of which is hereby incorporated by reference herein. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is incorporated by reference herein. Additional orthopaedic implants are disclosed in U.S. Pat. No. 6,176,880 and U.S. Pat. No. 6,793,676, both entitled "Tissue Grant Construct for Replacement of Cartilaginous Structures" and U.S. patent application Ser. No. 09/767,345 now abandoned, which are incorporated by reference herein.

Some of the orthopaedic implants disclosed in the above patent and patent applications cited in the preceding paragraph have a flat sheet of material that may include an extracellular matrix (ECM) such as small intestine submucosa. Some of the implants include additional material, such as a wedge of material on a sheet of material; the wedge and sheet may both include ECM material such as small intestine submucosa. The present invention addresses the need to deliver such implants to an intra-articular site. However, it should be understood that the present invention is not limited to use with the implants disclosed in those patent applications unless expressly called for in the claims; the present invention can be applicable to other implants as well.

The slide of the present invention can also be used to deliver an orthopaedic implant to a location outside of the intra-articular space of a joint site. For example, the instrument of the present invention can be used to deliver an orthopaedic implant to the area of the rotator cuff of the shoulder joint site. Unless expressly limited in the claims, "joint site" as used herein is intended to include the intra-articular space and other areas near the bones comprising a joint. "Damaged joint site", unless expressly limited in the claims, is intended to mean such a joint site that requires surgical repair, whether due to injury, degeneration or disease.

In addition, although the illustrated embodiments are particularly useful in delivering orthopaedic implants to damaged joint sites, the invention can also be applied to the delivery of other implants to other damaged tissue sites. "Damaged tissue site", unless otherwise expressly limited by the claims, is intended to mean a site within the body with damaged soft or bony tissue that requires repair, whether due to injury, degeneration or disease. And "implant", unless otherwise expressly limited by the claims, is intended to include orthopaedic implants as defined above and other devices intended to be implanted at a damaged tissue site for the approximation, repair or regeneration of native tissue at the damaged tissue site. An implant may comprise a tissue scaffold, patch or graft (including autografts, allografts and hetergrafts), for example. Moreover, "implant" and "orthopaedic implant" are intended to include such devices either alone or in combination with bioactive agents, biologically-derived agents, cells, a biological lubricant, a biocompatible synthetic or a biocompatible inorganic material, for example.

The device of the present invention comprises a slide for delivering an implant, such as those described in the preceding two paragraphs, to a damaged tissue site in the human body. The implant may be an orthopaedic implant, and the damaged tissue site may be a damaged joint site. The damaged joint site may for example be the knee, where the slide can be used to deliver an orthopaedic implant for use in approximating, repairing or regenerating a diseased or damaged meniscus. FIG. 41 illustrates the use of one embodiment of the present invention in delivering an orthopaedic implant to an intra-articular site in the knee. The damaged joint site may be in other locations in the body, such as the temporomandibular joint, between vertebrae, or any site where intra-articular fibrocartilage is in need of repair, approximation or regeneration.

A first embodiment of a suitable slide 10 is illustrated in FIGS. 1-5, 37 and 40. The slide 10 has a proximal end 12, a distal end 14 and an elongate longitudinal slide portion 16 extending between the proximal end 12 and distal end 14. In the first illustrated embodiment, the longitudinal slide portion 16 comprises slide surface 13 that is substantially flat in transverse cross-section. In longitudinal profile, as shown in FIG. 4, the first illustrated slide 10 has a straight portion 15 at its proximal end 12 and a curved portion 17 at its distal end 14.

The first illustrated slide 10 has side walls 18, 20 along the length of the longitudinal slide portion 16 between the proximal and distal ends 12, 14. The side walls 18, 20 are integral with the slide surface 13 of the longitudinal slide portion 16, and extend upward from the slide surface 13, generally parallel to each other and perpendicular to the slide surface 13. There are top walls 22, 24 integral with the side walls 18, 20 that extend the lengths of the side walls 18, 20 and over portions of the slide portion 16. Together, the side walls 18, 20 top walls 22, 24 and portions of the longitudinal slide portion 16 underlying the top walls 22, 24 define elongate channels 26, 28 along the edges of the longitudinal slide portion 16. The side walls 18, 20, top walls 22, 24 and channels 26, 28 follow the overall longitudinal profile of the longitudinal slide portion 16.

The bottom surfaces 30, 32 of the top walls 22, 24 are spaced from the slide surface 13 of the longitudinal slide portion 16 at a distance $d_1$ shown in FIG. 5, defining the height of each channel 26, 28. The height of each channel $d_1$ is generally slightly greater than the thickness of the edges of the orthopaedic implant 40 (shown in FIG. 37, for example), so that the edges of the implant 40 can be received in the channels 26, 28. Preferably, the channel height is such that the implant can slide down the slide surface 13 and not fall off of the slide along its travel. The channel height $d_1$ may be, for example, 0.5-5 mm. In the illustrated embodiments, the channel height $d_1$ is the same for both channels 26, 28, although it should be understood that each channel may have a different height if the implant is asymmetrical.

The slide 10 has an overall transverse dimension $d_2$ shown in FIG. 5. If the slide 10 is to be used in arthroscopic surgery, the greatest width $d_2$ of the slide should correspond with the size of the common surgical entry. For use in arthroscopy, the greatest width $d_2$ of the slide 10 would generally be on the order of 5-20 mm. However, it should be understood that these and other dimensions are provided by way of example only; the present invention is not limited to any particular dimension unless expressly set forth in the claims. In addition, although the slide of the present invention is useful in arthroscopic surgical procedures, the slide of the present invention can also be used in mini-arthrotomies and in open surgery as well. Where the slide of the present invention is referred to as an "arthroscopic" slide herein, the reference is intended to indicate that the slide is sized so that it is capable of being introduced arthroscopically to the damaged joint site.

A second embodiment of a slide, designated 10A, is illustrated in FIGS. 6-10 and 38. Like reference numbers have been used for parts corresponding to those described above for the first embodiment. The second illustrated slide 10A has the additional feature of a plurality of through-holes 34 extending through the entire thickness portion defining the slide surface 16 at the distal end 14. As illustrated in FIG. 38, the through-holes 34 are provided so that an orthopaedic implant 40 can be temporarily attached to the slide 10A using suture or the like, shown at 42 in FIG. 38. To facilitate connection and removal of the implant, the top walls 22, 24 may have indents or openings aligned with the through holes 34.

The second illustrated slide 10A also has a trapezoidal cut out 35 at its distal end 14, shown in FIGS. 6-8. Although this cut out 35 is illustrated in combination with the through-holes 34, the cut out 35 and through-holes 34 need not be used together. Use of such a cut out 35 has several possible advantages, regardless of whether through-holes 35 are provided. The cut out 35 can serve as a cutting guide for the surgeon to resect the damaged tissue. The cut out 35 also allows for better visualization of the defect site so that optimal positioning of the implant can be made; for example, the surgeon can place the cut out 35 over the defect site, and slide the implant down the slide surface 13 until the implant is at the cut out 35. If several possible sizes of implants are available, several slides could be provided, each with a cut out sized and shaped to match an implant size. The surgeon can then use the slides to determine the most appropriate size of implant for the defect site (that is, the slides could be used for trailing). The cut out 35 may be sized to mimic the size and shape of the implant.

A third embodiment of a slide, designated 10B, is illustrated in FIGS. 11-15, 39 and 41. Like reference numbers have been used for parts corresponding to those described above for the first embodiment. The third illustrated slide 10B differs from the first illustrated embodiment primarily in the shape of the longitudinal slide portion 16. In the third embodiment, the longitudinal slide portion 16 comprises two integral surfaces 44, 46 that meet at an angle $\alpha$ shown in FIG. 15. In the embodiment of FIGS. 11-15, the angle $\alpha$ is 90°. However, it should be understood that this angle is provided by way of example only; the invention is not limited to this angle unless expressly called for in the claims. The angle $\alpha$ can be less than 90° or greater than 90°, as in the slide 10C illustrated in FIGS. 16-20.

The fourth embodiment of the slide 10C of the present invention, illustrated in FIGS. 16-20, is substantially similar to the third embodiment of FIGS. 11-15, and the description of the third slide 10B applies to the fourth slide 10C as well. In the drawings, like reference numbers have been used for parts corresponding to those described above for the first and third embodiments.

A fifth embodiment of a slide is illustrated in FIGS. 21-25 and is designated 10D. In the embodiment of FIGS. 21-25, the longitudinal slide portion 16 is curved in transverse cross-section to define an elongate curved slide surface 50 to receive the orthopaedic implant. The elongate channels 26, 28 of the fifth slide 10D are defined by walls 52, 54 that are integral with the curved slide surface 50 and curve inward toward each other and then toward the elongate curved slide surface 50. The walls 52, 54 defining the channels 26, 28 have inner surfaces that are spaced a distance $d_1$ from the slide surface 50. As in the above-described embodiments, the dimension $d_1$ may be slightly greater than the thickness of the edges of the implant to allow the implant to be moved along the slide surface 50 while also being retained on the slide surface. The slide 10D also may have an overall maximum transverse dimension $d_2$ that is small enough to allow the slide to be inserted through a standard incision for minimally invasive surgery, or through a standard cannula used in such minimally invasive surgical procedures.

As can be seen from a comparison of the embodiments of FIGS. 1-10 with the embodiments of FIGS. 11-25, the curved portions 17 of the slides of the illustrated embodiments can either curve downward, as shown in FIGS. 1-10, or curve upward, as shown in FIGS. 11-25. It should be understood that the slides could also be completely straight with no curved portions. Additionally, note that similar to the embodiment illustrated in FIGS. 16-20, the slide could be pointed sideways as well as downward. Accordingly, unless a specific profile is set forth in a claim, the invention should not be construed as being limited to a specific profile.

In all of the illustrated embodiments of the slide 10-10D, the slide surfaces 13, 44, 46, 50 may be smooth so that the orthopaedic implant can be moved along the surfaces without damage. All of the illustrated embodiments can be made out of standard medical grade material, such as medical grade plastic for example. A suitable commercially available medical grade plastic is ABS plastic. The illustrated embodiments could be molded, machined or produced through a combination of molding and machining, although molding is expected to be preferable from a cost perspective.

In use, all of the illustrated embodiments of the slide 10-10D can be inserted through a typical arthroscopic surgical portal such as that illustrated at 60 in FIG. 41. FIG. 41 illustrates use of the third embodiment 10B of the arthroscopic slide, although it should be understood that the following description can be applied to all of the illustrated embodiments. However, as indicated above, the present invention is not limited to use of the slides in an arthroscopic procedure unless expressly set forth in the claims. In addition, the slides of the present invention are not limited to any particular size or dimension, and need not be sized or dimensioned for arthroscopic use unless expressly called for in the claims.

FIG. 41 illustrates a damaged or diseased lateral meniscus 61; the drawing shows the meniscus 61 after a partial menisectomy has been performed to create a gap shown at 62. To fill the gap, an orthopaedic implant is delivered to the site of the gap 62. In FIG. 41, the orthopaedic implant, designated 64, is generally wedge-shaped, with upper and lower planar cover portions (shown at 65 and 67 in FIG. 39) with a wedge (shown at 69 in FIG. 39) between them. The wedge can comprise, for example, a reticulated ECM foam that has been seeded with chondrocytes, and the cover can comprise, for example, an ECM laminate, with, for example, 8-50 layers of small intestine submucosa laminated together. The third embodiment 10B of the slide may be selected for use with such an orthopaedic implant so that the upper cover portion 65 can be placed on one of the slide surfaces 44 and the lower cover 67 on the other slide surface 46, with the edges of the cover portions received in the elongate channels or slots 26, 28, as shown in FIG. 39.

The wedge shaped portion 69 is thus held between the cover portions 65, 67 on the two slide surfaces 44, 46, below the plane 70 of the top of the slide and above the plane 72 of the bottom of the slide. Containing the orthopaedic implant within the walls and slide surfaces of the slide protects the implant as the implant is moved to the intra-articular space where the implant is to be secured. This advantage is possible with all of the illustrated embodiments of the slide of the present invention; it is expected that one would select the shape of slide that will best protect the particular shape of implant. The slides 10-10D of the present invention provide the surgeon with options in moving an implant from outside of the patient's body, through an arthroscopic port and into an intra-articular space. First, the surgeon can opt to place the orthopaedic implant at the distal end 14 of the slide 10B. The surgeon can place the implant (e.g. implant 40 or 64) at the distal end 14 of the slide with parts of the implant constrained within the channels 26, 28, as shown for example in FIG. 39 with a wedge shaped implant. If the slide 10-10D has through-holes of the type shown at 34 in the embodiment of FIGS. 6-10, the surgeon can loosely attach the implant to the distal end of the slide surface 13 using suture 42 or the like as shown in FIG. 38. The distal end 14 of the slide, with the orthopaedic implant, is then inserted through the arthroscopic portal 60 and guided into the intra-articular space, such as the meniscal space shown in FIG. 41. Since the implant is contained between the planes 70, 72, the implant is protected from abrasive contact with any tissue as the slide is manipulated through the portal 60 and through the patient's native tissue. Thus, the orthopaedic implant can be delivered to the intra-articular space adjacent the fibrocartilage defect through a minimally-invasive surgical technique without damaging the orthopaedic implant. Once the implant and distal end 14 of the slide are properly positioned in the intra-articular space, the surgeon can move the implant off of the slide and into the defect site, such as the gap 62 remaining in the meniscus 61 after the partial menisectomy shown in FIG. 41.

It should be understood that the angle of entry illustrated in FIG. 41 is provided as an example only. The arthroscopic portal can be an anterior one as shown at 60A in FIG. 42.

To move the implant from the slide, the surgeon can insert standard surgical instruments through other portals to the intra-articular space to cut any suture 42 securing the implant to the slide, to move the orthopaedic implant into its final position, and to secure the orthopaedic implant to native tissue. The surgeon may also use the device disclosed in U.S. patent application Ser. No. 10/609,768 entitled "Implant Stabilizing Instrument, Kit and Method," filed concurrently herewith by (Andrew M. Jacobs, Carolyn K. Day, Rhonda B. Clarke, Herbert E. Schwartz, John W. Kemppainen, Prasanna Malaviya and Anthony D. Zannis), which is incorporated by reference herein in its entirety. The instrument, kit and method disclosed in that patent application may be used to move and stabilize the implant while securing the implant to the native tissue.

The surgeon can also opt to insert the distal end 14 of the slide through the arthroscopic portal 60 and into the intra-articular space before placing the orthopaedic implant on the slide. Considering FIG. 41, after the surgeon has confirmed that the distal end 14 of the slide 10B is properly positioned in the intra-articular space in proper proximity to the defect, for example gap 62 in meniscus 61, the surgeon can place the orthopaedic implant 64 on the slide surfaces (e.g. 44, 46) with the edges of the implant within the elongate channels 26, 28, as shown in FIG. 41. The surgeon can then use another surgical implement to move the implant distally along the slide surfaces until the implant is at the distal end 12 of the slide. The surgeon can continue to move the implant off of the slide and into the gap 62 in the meniscus 61 and then attach the orthopaedic implant to the native tissue. FIG. 37 illustrates movement of an implant 40 from a proximal position (shown in phantom) to a distal position along the slide surface 13 using the first illustrated slide 10.

It will be appreciated that the surgical method described above can also be used in delivering implants to other damaged tissue sites in the patient's body. In addition, substantially the same surgical method can be used for mini-arthrotomies and open surgeries.

Examples of possible surgical instruments for use in moving the implants either along the slide surfaces 13, 44, 46, 50 or off of the distal end 14 of the slide 10-10D are illustrated in FIGS. 26-36 and 40. Each instrument of FIGS. 26-36 and 40 comprises an elongate guide member. The elongate guide member may comprise a simple thin strip of flexible material, as shown at 80 in FIGS. 26-27. Generally, such a guide member 80 may have a thickness shown at $t_1$ in FIG. 27 that is slightly less than the channel height d and a width shown at $w_1$ in FIG. 26 that is slightly less than the transverse distance $d_2$ between the inner surfaces of the walls 18, 20 so that the surgeon can slide the guide member 80 distally and proximally in the channels 26, 28. As shown in FIG. 40, the surgeon can push the proximal end of the guide member 80 to push the orthopaedic implant 40 distally along the slide surface 13 and off of the distal end 14 of the slide 10.

Another embodiment of an elongate guide member is designated 80A in FIGS. 28-29. In this embodiment, the distal end 82 of the guide member has a wedge shaped portion 84. The wedge shaped portion 84 narrows as it nears the distal end. When using the embodiment of FIGS. 28-29, the surgeon pushes the elongate guide member 80A in a distal direction. As the wedge shaped portion 84 reaches the orthopaedic implant 40, the wedge shaped portion 84 travels over the top surface of the implant and then frictionally engages the implant to move the implant in the distal direction. Thus, with the embodiment of FIGS. 28-29, force is not applied solely to the edge of the implant, but to an area of the surface of the implant to move the implant to the intra-articular space.

For all the embodiments of FIGS. 28-33, the dimensions $t_1$ and $w_1$ may be like those described above for the embodiment of FIGS. 26-27 so that the surgeon can slide the guide members while the walls 18, 20, 22, 24 constrain movement of the guide members to sliding in the proximal-distal direction.

FIGS. 30-31 illustrate another embodiment of an elongate guide member 80B. In this embodiment, the distal end 82B of the guide member 80B has an opening 86 between two spaced end tines 88, 90. Each of the end tines 88, 80 has a textured undersurface; in FIG. 31, the texture is illustrated as a plurality of nubs 92. The guide member 80B of FIGS. 30-31 can be dimensioned and positioned so that the nubs 92 engage the surface of the orthopaedic implant while the implant is held by the slide and then used to move the implant distally off of the slide. In addition, the nubs and guide member can be used to hold the implant in position at the defect site. With the implant held by the guide member, the surgeon can fixate the implant by applying a suitable apparatus or material (e.g. suture or a tack) through the opening 86.

Figure 33:
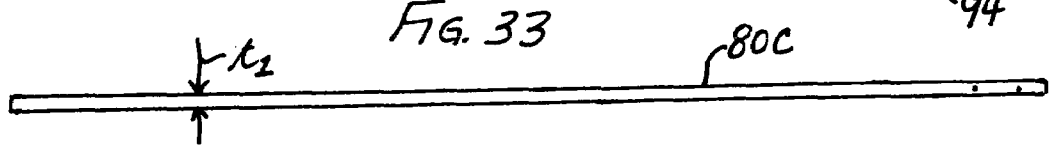
FIG. 33 is a side elevation of the elongate guide member of FIG. 32.
Figure 34:
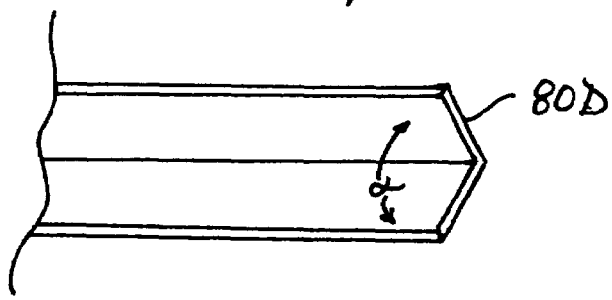
FIG. 34 is a perspective view of an end of a fifth embodiment of an elongate guide member that may be used with the arthroscopic slide of the present invention.

FIGS. 32-33 illustrate another embodiment of an elongate guide member 80C. In this embodiment, the distal end 82C of the guide member 80C has a pair of joined through-holes 94. The distal end of the guide member 80C can be used to hold the implant in place and allow for another surgical instrument, such as a pair of suturing needles, to be inserted through the holes 94 to fixate the implant at the defect site while the implant is being held by the guide member 80C.

Figure 35:
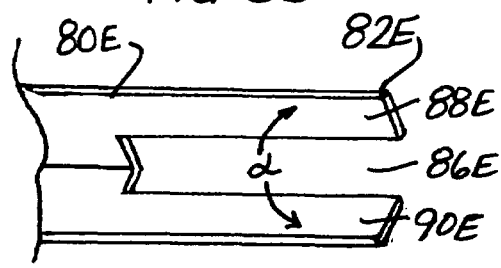
FIG. 35 is a perspective view of an end of a sixth embodiment of an elongate guide member that may be used with the arthroscopic slide of the present invention.
Figure 36:
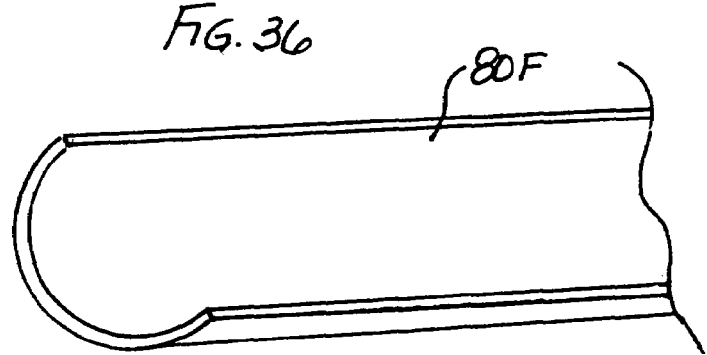
FIG. 36 is a perspective view of an end of a seventh embodiment of an elongate guide member that may be used with the arthroscopic slide of the present invention.
Figure 43:
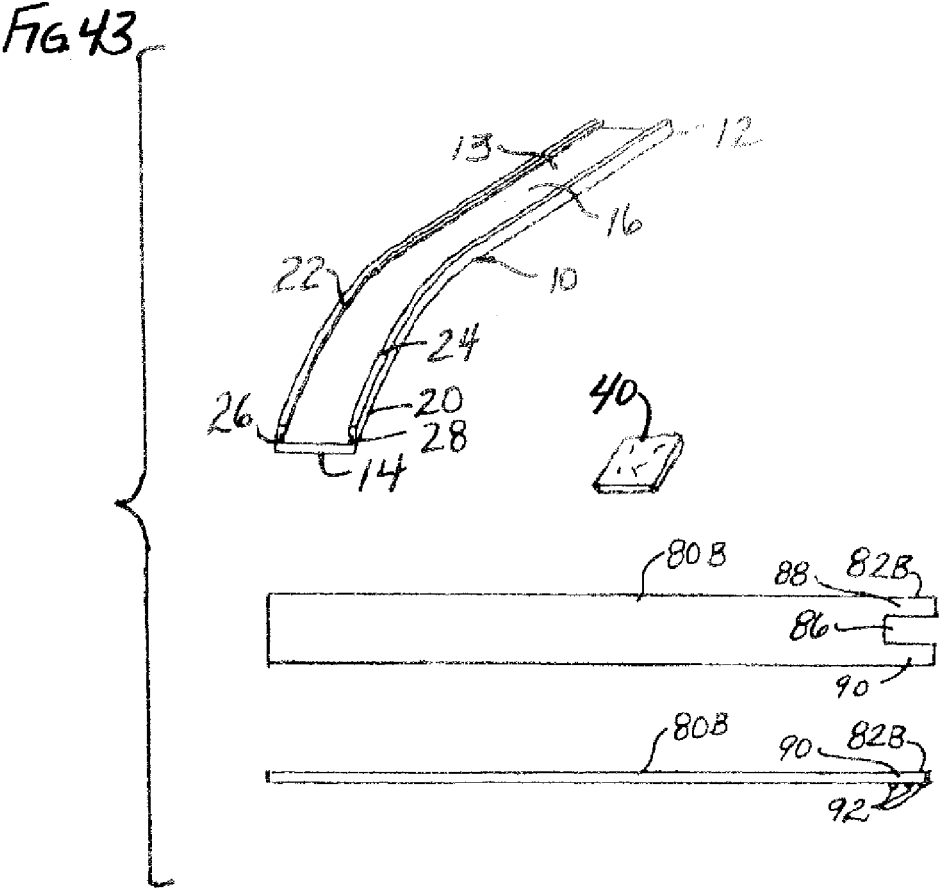
FIG. 43 is a view of a kit including a perspective view of the slide of the type shown in FIG. 1 with a top plan view and side elevation of an elongate guide member of the type shown in FIGS. 30-31 and with a perspective view of an orthopaedic implant.
Figure 44:
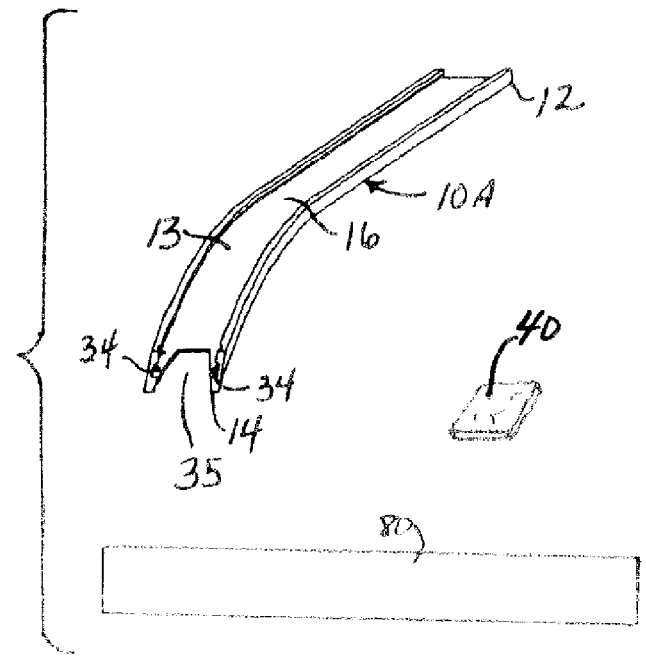
FIG. 44 is a view of a kit including a perspective view of the slide of the type shown in FIG. 6 with a top plan view of an elongate guide member of the type shown in FIGS. 26-27 and with a perspective view of an orthopaedic implant.
Figure 45:
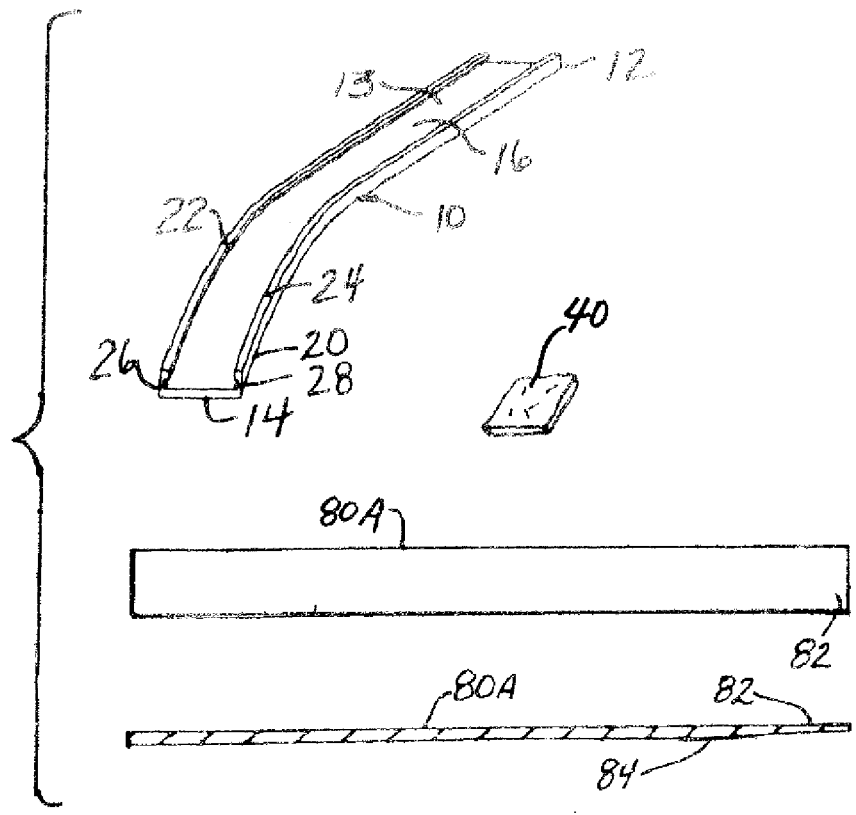
FIG. 45 is a view of a kit including a perspective view of the slide of the type shown in FIG. 1 with a top plan view and longitudinal cross-section of an elongate guide member of the type shown in FIGS. 28-29 and with a perspective view of an orthopaedic implant.
Figure 46:
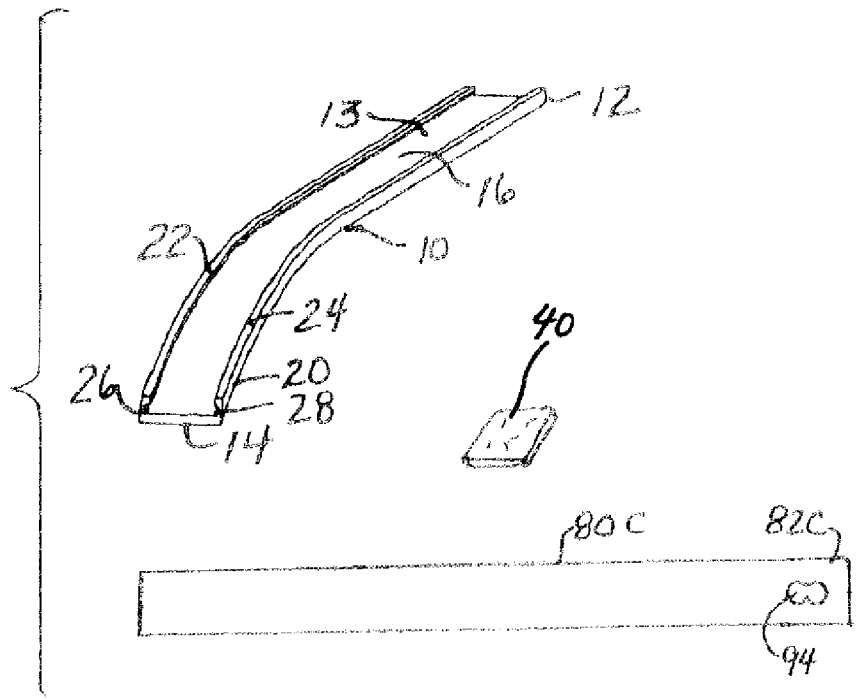
FIG. 46 is a view of a kit including a perspective view of the slide of the type shown in FIG. 1 with a top plan view of an elongate guide member of the type shown in FIGS. 32-32 and with a perspective view of an orthopaedic implant.

The elongate guide member can be shaped to conform to the shape of the slide portion 16. For example, for a slide of the type shown at 10B and 10C in FIGS. 11-20, 39 and 41, a suitable guide member can be shaped like those shown in FIGS. 34-35 at 80D and 80E. For a slide of the type shown at 10D in FIGS. 21-25, a suitable guide member can be shaped like that shown in FIG. 36 at 80F. The elongate guide members of FIGS. 34-36 can have features like those described above for the embodiments of FIGS. 28-33; for example, as shown in FIG. 35, the distal end 82E of an angled guide member 80E could have an opening 86E between two end tines 88E, 90E, similar to that shown in FIGS. 30-31.

Alternatively, the elongate guide member could be shaped differently from the slide so that the elongate guide member essentially forms a protective cover over the slide.

All of the elongate guide members 80-80E can be made of standard medical grade material, such as plastic for example. A suitable example of medical grade plastic is Delrin. The elongate guide members may be made in any economical manner, such as by molding or cutting from a sheet form of the material. For use with the illustrated slides with curved portions 17, the elongate guide members should be flexible enough to follow the curve of the slide member. For the embodiments that allow for use of the guide member to hold the implant in place while the implant is being fixated, it may be desirable to provide some stiffening reinforcements to the distal end of the elongate guide member. Part or all of the elongate guide members could include a shape-memory material such as the Nitinol alloy of nickel and titanium.

The slides 10-10D and elongate guide members 80-80E could be provided as parts of surgical kits. A surgical kit could include one type of slide and a mating type of elongate guide member. A surgical kit could include a plurality of different types of slides, with or without mating elongate guide members, as illustrated in the examples of surgical kits shown at 100, 102, 104 and 106 in FIGS. 43-46. Any of the surgical kits 100, 102, 104, 106 described could also be provided with one or more orthopaedic implants 40, as shown in FIGS. 43-46.

It should also be understood that if both a slide and an elongate guide member are provided in a surgical kit, such as surgical kits 100, 102, 104, 106, 108 of FIGS. 43-46, the complementary structural features described above could be identified with either of the elements. For example, the walls defining the elongate channels could be associated with the elongate guide member instead of with the slide so that the edges of the slide are received within complementary channels of the elongate guide member.

Alternative instruments for delivering an implant to a damaged tissue site are disclosed in the following U.S. patent applications, filed concurrently herewith and incorporated by reference herein in their entireties: U.S. Provisional Pat. App. Ser. No. 10/742,020 entitled "Instrument for Delivery of Implant," filed concurrently herewith by Andrew M. Jacobs, Carolyn K. Day, Rhonda B. Clarke, Herbert E. Schwartz, John W. Kemppainen, Prasanna Malaviya and Anthony D. Zannis, and U.S. patent application Ser. No. 10/610,288 entitled "Implant Delivery Instrument," filed concurrently herewith by Anthony D. Zannis, Thomas S. Camino, John W. Kemppainen, Herbert E. Schwartz and Danny E. McAdams.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A system for delivering an implant to a damaged tissue she in the body of a patient, the system comprising:
   an implant comprising a sheet of biocompatible material having a top surface and an opposite bottom surface; and
   a slide having a proximal end, a distal end and an elongate longitudinal slide portion between the proximal and distal ends;
   the slide having walls defining spaced longitudinal channels along the longitudinal slide portion;
   the implant being positioned on the longitudinal slide portion of the slide and between the longitudinal channels with the bottom surface of the implant in contact with the longitudinal slide portion of the slide and with at least a portion of the top surface of the implant exposed between the spaced longitudinal channels, the implant having a leading edge and a trailing edge, the top surface extending substantially between the leading edge and the trailing edge;
   the system further comprising an elongate guide member, wherein the elongate guide member and longitudinal channels are complementary so that parts of the elongate guide member are receivable in the longitudinal channels, wherein the elongate guide member is slidable in the longitudinal channels in a proximal-distal direction and wherein the longitudinal channels constrain movement of the elongate guide member to sliding in the proximal-distal direction;
   wherein the channels of the slide and the elongate guide member are sized and shaped so that a portion of the implant can be received within each channel;
   wherein at least a portion of the elongate guide member extends past one of the edges of the implant and overlies and contacts at least a portion of the top surface of the implant; and
   wherein the elongate slide portion, channels and walls defining the channels of the slide have a longitudinal profile including a curved portion at the distal end and a straight portion at the proximal end; and
   wherein the implant comprises an orthopaedic implant and the damaged tissue site comprises a damaged joint site.

2. The system of claim 1 wherein the slide has a maximum transverse dimension between the walls defining the longitudinal channels sized so that the distal end of the slide can be introduced arthroscopically to the damaged tissue site.

3. The system of claim 2 wherein the maximum transverse dimension of the instrument is 20 mm.

4. The system of claim 1 wherein the longitudinal slide portion comprises a surface that is substantially flat in transverse cross-section.

5. The system of claim 1 wherein the longitudinal slide portion comprises two surfaces meeting at an angle in transverse cross-section.

6. The system of claim 1 wherein the longitudinal slide surface comprises a curved surface in transverse cross-section.

7. The system of claim 1 wherein the longitudinal slide portion is smooth from the proximal end to the distal end of the device so that the implant can slide along the longitudinal slide portion without damage to the implant.

8. The system of claim 1 wherein the slide is open between the walls defining the spaced longitudinal channels.

9. The system of claim 1 wherein the elongate guide member has a distal end including a textured surface in contact with the surface of the implant.

10. The system of claim 1 wherein the elongate guide member has a distal end, and wherein the distal end of the elongate guide member is wedge-shaped in longitudinal cross-section, wherein the wedge-shaped portion of the elongate guide member is in contact with the surface of the implant.

11. The system of claim 1 wherein the implant includes naturally occurring extracellular matrix material.

12. The system of claim 1 wherein the implant includes a synthetic biocompatible material.

13. The system of claim 1 wherein the damaged joint site comprises an intra-articular site.

14. A surgical kit for delivering an implant to a damaged tissue site in a patient's body, the kit comprising:
- an elongate guide member having a proximal end and a distal end; and
- a slide for delivering an orthopaedic implant to the damaged tissue site, the slide comprising a proximal end, a distal end, a pair of spaced edges extending from the proximal end to the distal end and a longitudinal slide portion extending between the spaced edges between the proximal and distal ends;
- the distal portion of the longitudinal slide portion having a pair of spaced tangs and an edge extending along the tangs and transversely between the tangs, the edge defining a trapezoidal opening at the distal end of the slide, one of the tangs being along one of the edges of the longitudinal slide portion, the other tang being along the other edge of the longitudinal slide portion, the trapezoidal opening lying between the spaced edges of the longitudinal slide portion;
- wherein each tang includes an edge defining a through-hole extending through the tang;
- wherein the elongate guide member has a maximum transverse dimension so that the distal end of the elongate guide member can be introduced arthroscopically to the damaged tissue site;
- wherein the slide has a maximum transverse dimension so that the distal end of the slide can be introduced arthroscopically to the damaged tissue site;
- wherein the elongate guide member and slide have complementary structures to allow the elongate guide member and slide to be connected to each other while allowing relative movement between the elongate guide member and slide in the proximal-distal direction while the elongate guide member and slide are connected.

15. The surgical kit of claim 14 wherein the complementary structures comprise channel members and edges sized to fit within the channel members.

16. The surgical kit of claim 15 wherein the channel members are associated with the slide, the channel members extending along each side of the slide along the length of the longitudinal slide portion.

17. A system for repairing a fibrocartilage defect in an intra-articular space in a patient's body, the system comprising:
- a wedge-shaped orthopaedic implant comprising biocompatible material;
- an elongate guide member having a proximal end and a distal end; and
- a slide for delivering the orthopaedic implant to the damaged tissue site, the slide comprising a proximal end, a distal end and a longitudinal slide portion between the proximal and distal ends, the longitudinal slide portion including a distal portion at the distal end of the slide, the distal portion having two sides meeting at an angle along an apex, a top and a bottom;
- wherein the wedge-shaped implant is positioned between a plane at the top of the distal portion of the slide and a parallel plane at the bottom of the distal portion of the slide;
- wherein the elongate guide member has a maximum transverse dimension so that the distal end of the elongate guide member can be introduced arthroscopically to the intra-articular space;
- wherein the slide has a maximum transverse dimension so that the distal end of the slide can be introduced arthroscopically to the intra-articular space;
- wherein the elongate guide member and slide have complementary structures to allow the elongate guide member and slide to be connected to each other while allowing relative movement between the elongate guide member and slide in the proximal-distal direction while the elongate guide member and slide are connected so that the elongate guide member can be used to move the orthopaedic implant off of the slide; and
- wherein the distal end of the elongate guide member includes two sides meeting at an angle along an apex and a pair of spaced tines extending distally from the sides, the spaced tines lying in planes meeting at an angle, the planes of the tines, the sides of the distal end of the elongate guide member and sides of the slide meeting at substantially the same angle.

* * * * *